United States Patent [19]

Seim et al.

[11] Patent Number: 5,028,538
[45] Date of Patent: Jul. 2, 1991

[54] PROCESS FOR THE PRODUCTION OF L-CARNITINE AND ITS DEIVATIVES

[75] Inventors: Hermann Seim; Heniz Loester; Rainer Claus; Hans-Peter Kleber; Erich Strack, all of Leipzig, German Democratic Rep.

[73] Assignee: Sigma Tau Industries Farmaceutiche Riunite S.p.A., Rome, Italy

[21] Appl. No.: 349,929

[22] Filed: May 9, 1989

Related U.S. Application Data

[63] Continuation of Ser. No. 665,765, Oct. 29, 1984, abandoned.

[30] Foreign Application Priority Data

Nov. 3, 1983 [DD] German Democratic Rep. .................................. 2562812

[51] Int. Cl.$^5$ .......................... C12R 1/19; C12P 13/00
[52] U.S. Cl. .................................. 435/128; 435/252.8; 435/280
[58] Field of Search ...................... 435/128, 252.8, 280

[56] References Cited

U.S. PATENT DOCUMENTS 4,650,759 3/1987 Yokozeki et al. .................... 435/128
4,708,936 11/1987 Kulla et al. .......................... 435/128

OTHER PUBLICATIONS

*Chemical Abstracts*, vol. 98, No. 15, abstract 122551z, Apr. 11, 1983; Seim et al., "Reductive Metabolism of L-carnitine . . . by Escherichia coli".

*Chemical Abstracts*, vol. 96, No. 21, abstract 177676h; May 24, 1982; Seim et al., "Formation of γ-butyrobetain . . . by Proteus vulgaris".

Seim et al., "Stimulation of Anaerobic Growth of *Salmonella typhanurium* by Reduction of L-Carnitine, Carnitine Derivatives and Structure-Related Trimethylammonium Compounds"; *Arch. Microbiol.* 132: 91-95 (1982).

Seim et al., "Reduktiver Stoffwechsel des L-Carnitins und strakturverwandter Trimethylammonium verbindungen in *Escherichia coli*"; *Acta Biol. Med. Germ.*, vol. 41, 11: 1009-1018 (1982).

Different Carnitine Acyltransferases in Calf Liver BBA 280, pp. 422-433 by Helge Erik Solberg.

Primary Examiner—Herbert J. Lilling
Attorney, Agent, or Firm—Ladas & Parry

[57] ABSTRACT

The invention relates to a process for the L(−)-carnitine biochemical production, in an economically favorable way.

This new process is technically achievable with easily available raw, materials in simple reaction conditions and with not complicated substance separation techniques.

This process is carried out with bacteria that stereospecifically hydrates crotonobetaine to L(−)-carnitine.

8 Claims, No Drawings

PROCESS FOR THE PRODUCTION OF L-CARNITINE AND ITS DEIVATIVES

This is a continuation of co-pending application Ser. No. 06/665,765, filed on Oct. 29, 1984, now abandoned.

The present invention relates to a process for the production of optically active L(−)-carnitine(R-configuration) from an optically inactive precursor.

L-carnitine (3-hydroxy -4-trimethylaminobutyrate) is normally present in the organism where it exerts the role of activated long-chain free fatty acids' carrier, through the mitochondrial membrane. Since the mitochondrial membrane is impermeable to the acyl CoA's derivatives, the long-chain free fatty acids can cross it only when the esterification with L-carnitine has taken place. The importance of using L(−)-carnitine for therapeutical use has recently been underlined. ("Carnitine biosynthesis. metabolism, and functions" Editors: R. A. Frenkel and J. D. Mc Garry Academic Press 1980).

Since the needed quantity of L-carnitine was not available, it was often substituted with the DL-carnitine racemate, obtainable by total chemical synthesis. But the DL-carnitine, which contains the D(+) isomer, caused certain side effects which had not taken place using L(−)-carnitine (Curr. Ther. Res. 28 (1980), 195-198).

It is also known that the transferases necessary for the L(−)-carnitine formation, the carnitine acetyl-transferase (EC 2.3.1.7) and the carnitine palmitoyl-transferase (EC 2.3.1.21), are specific for the L(−) form, whereas the D(+) isomer is a competitive inhibitor of these two transferases.

Administration of D-carnitine can, moreover, create a decrease of L(−)-carnitine in the cardiac muscle or in the skeletal muscle, as has been demonstrated on laboratory animals (guinea-pigs) (Life Sciences 28 (1981) 2931-2938). The symptoms of human hyperthyrosis which had improved after L-carnitine treatment, worsened drastically with D-carnitine (Endokrinologie, 38, (1959) 218-225), thus for patients' treatment only L(−)-carnitine can presently be used. This is also and especially valid in the case of patients having chronical kidney failure who have no possibility of actively eliminating the D(+) isomer.

Hemodialysis induces an L-carnitine secondary deficiency since it is eliminated in the dialysate, given its low molecular weight (161.2). The oral administration or the addition of L(−)-carnitine in the dialysis solution has avoided carnitine decrease in the patients.

In the case of hyperlipoproteinemia, widespread in industrialised countries, a significant decrease of the levels of plasma risk factors, triglycerides and cholesterol, has been reached with L(−)-carnitine (Lancet II (1978) 805-807). Similar effects could have been obtained using acylcarnitine (DE-OS 2903579).

DESCRIPTION OF THE PRIOR ART

L(−)-carnitine has been isolated from meat extracts with a complicated purification procedure.

In the '50's chemical synthesis were perfected, though only DL-carnitine could be obtained.

Up till now, the isomer L(−)-carnitine has been obtained by the racmate's resolution with fractional crystallisation of carnitine's salts with optically active acids. Various carnitine derivatives have been used, such as carnitine-nitrile, carnitinamide or even carnitine inner salt itself.

As optically active acids, tartaric, camphoric and camphor-sulphonic acids were used (p.e. DD-PS 23217; DD-PS 93 347; DE-OS 2927672).

DL-carnitine has also been resolved with specific L(−)-transferases.

But, since for the production of one mole of L(−)-carnitine, at least one mole of acyl CoA was needed, this procedure turned out to be too expensive to apply industrially.

All the other chemical synthesis with subsequent racemate resolution have the ulterior disadvantage that from synthesised DL-carnitine not more than 50% of the wanted isomer can be isolated.

This problem has been overcome with enzymatic stereospecific synthesis with achiralic precursors.

The U.S. Pat. No. 4, 221,869 describes the production of L(−)-carnitine from dehydrocarnitine with carnitine dehydrogenase (EC 1.1.1.108) isolated from "*pseudomonas fluorescens*" using NAD as coenzyme,.though other enzymes are necessary, such as glucose dehydrogenase or alcohol dehydrogenase for the regeneration of NADH. Moreover, dehydrocarnitine is very instable and it spontaneously decomposes in acetonyltrimethylammonium and carbon dioxide.

The Patent application DE-OS 3123975 describes L(−)-carnitine production from γ-butyrobetaine with γ-butyrobetaine hydroxylase (EC 1.14.11.1) isolated from "*Neurospora crassa*" mould. During this hydroxylase reaction α-ketoglutaric acid and a reducing agent (i.e. ascorbate) must be added to the incubation medium.

To have the maximum yield of L(−)-carnitine, catalase is also needed. γ-butyrobetaine hydroxylase is obtained after mould growth, isolation and purification of its spores with detergents and mechanical or ultrasonic treatment. The precursors of the L(−)-carnitine biosynthesis are L(−)-methionine and L-lysine. Through the ε-N,N,N trimethyl lysine, ε-N,N,N trimethyl-β-hydroxy-lysine and N,N,N trimethylamino butyraldehyde intermediates, γ-butyrobetaine is formed. It is hydroxylated to L-carnitine by γ-butyrobetaine hydroxylase in presence of molecolar oxigen, α-ketoglutaric acid, ferrous ions and a reducing agent. Crotonobetaine is not an intermediate in the biosynthesis.

The invention's purpose is that of overcoming the disadvanages of the known methods of L(−)-carnitine production and to indicate a procedure that allows, in a favorably economical way, the biochemical production of the compound.

DESCRIPTION OF THE INVENTION

The invention describes the technically realisable procedures to produce L(−)-carnitine from easily available raw materials under simple reaction conditions and with not complicated intermediate separation techniques.

Until now the only notions were:

(1) L(−)-carnitine, D(+)-carnitine and crotonobetaine are metabolized to γ-butyrobetaine.

(2) the enterobacter growth stimulation depends on the γ-butyrobetaine formation, obtained by the crotonobetaine reduction. (Arch. Microbiol. 132 (1982), 91-95).

(3) The "clostridia-bacteria" are capable of reducing crotonic acid to butyric acid in anaerobic conditions. (FEBS Lett. 109, (1980) 244–246).

Surprisingly it was found that even some bacteria, in certain particular conditions, had been capable of stereospecifically hydrating crotonobetaine to L(−)-carnitine; a process which had not been observed in presence of γ-butyrobetaine in the incubation medium.

These bacterial strains were:

*Escherichia coli* (*E. coil* 044 K74; 055 K 59; 0 111 K58; 0 114 K90) Salmonella (*S. typhimurium* LT₂; *cottbus; anatum; newington*)

Proteus (*P. vulgaris; mirabilis*)
Shigella (*S. flexneri* 1a) .
Hafnia (*H. alvei* Biotyp A and B)
Clostridium (*C. kluyveri; sporogenes*)
Citrobacter (*C. freundii*).

According to the invention, to the bacteria growing on complex or minimal mediums, or to resting cells, crotonobetaine (4-N,N,N-triethylamino crotonic acid) or one of its salts, such as for example chloride, iodide, perchlorate, nitrate phosphate, or crotonobetaine amide, nitrile and aryl or alkyl ester is added.

After a certain period of incubation the L(−)-carnitine formed is isolated from the reaction medium.

The crotonobetaine concentration in the incubation medium was included between 10 μ moles and 5 moles/1. As described in tables V, VI, VII the quantity of L(−)-carnitine formed increased with the increase of crotonobetaine conoentration, but the percentual yield refered to the raw material decreased.

After the separation of the L(−)-carnitine from crotono betaine the latter may be used again.

The resting cells were incubated in a minimal culture medium with salt solutions, organic and inorganic buffer mixture which did not contain any C and/or N sources or of which the C and contents could not be used by the bacteria.

The incubation times were comprised between 3 hrs and 5 days. A preferred interval of time is 12 hrs–48 hrs.

The bacteria capable of hydrating crotonobetaine can grow on the more diverse complex culture mediums, solid or liquid, thus commercial nutritive mediums containing meat, yeast, malt and starch water extracts can be used, adding, in partially anaerobic conditions, C and/or N sources such as ammonium hydroxide, urea, alcohol, carbohydrates, organic acids including fatty acids. The cultures are grown in calibrated tubes, in anaerobic condition and without stirring.

The reduction of crotonobetaine to γ-butyrobetaine leads to a loss of substance for L(−)-carnitine synthesis, thus this reduction reaction is inhibited by adding electron acceptors of the anaerobic respiration and other substances. Non limiting examples of the invention are oxygen, nitrates, trimethylamine N-oxide and other N-oxides, dimethyl sulphoxide, glucose, fructose, saccarose, maltose and electron acceptors such as fumarate, crotonate and acrylate. (Tables II, III, IV).

The bacteria grown on commercial nutritive mediums, supplemented with meat broth or pancreatic peptone were able to hydrate crotonobetaine to L(−)-carnitine (table IX). The rate of L(−)-carnitine synthesis is increased, though, by inducing crotonobetaine hydroxylase, adding to the culture medium of growing bacteria, crotonobetaine, DL-carnitine, fractions of DL-carnitine enriched with D(+) (obtained by the chemical resolution of the racemate) or its derivatives (i.e. carboxylic esters, O-acylcarnitine or O-acylcarnitine esters).

Crotonobetaine, its salts or its derivatives. were prepared according to the following known proceedings:

1) Dehydration with sulphuric acid or acetic anhydride of DL-carnitine, D(+)-carnitine or D(+) enriched DL-carnitine, or alternatively elimination of the acid from the corresponding O-acyl DL-carnitine or O-acyl D carnitine.

2) Exhaustive methylation of the 4-ammino crotonate with methyl halogenides.

3) Reaction of trimethylamine with 4-halogen substituted crotonate.

A good separation of the L(−)-carnitine from non reacted crotonobetaine or from the formed γ-butyrobetaine. by ion-exchange cromatography ("Recent research on carnitine" Ed. G. Wolf, pg 11–21 (1965), US-PS 4,221,869; DE-OS 3123975) can only be carried out for small quantities.

L(−)-carnitine in larger quantities has been separated after reaction of the hydroxy group with the acyl chlorides of medium and long chain fatty acids.

The O-acyl carnitines formed can be extracted from the water phase with n-butanol or isobutanol (Biochim. Biophys. Acta 280, (1972), 422–433).

The O-acyl carnitines are obtained by evaporation of the organic phase. They can be used directly in the biochemical research, or hydrolyzed with ammonium hydroxide to L(−)-carnitine which is then utilized for therapeutical application.

The crotonobetaine which remains in the water phase is added back to the incubation medium.

The L(−)-carnitine formed was measured using the carnitine acetyltransferase after the addition of acetyl CoA with the DTNB method.

The excess presence of crotonobetaine from 10 to 100 does not disturb the L(−)-carnitine determination.

Some of the advantages of this procedure are:

1) By dehydration of the D(+)-carnitine or of the D(+) enriched DL-carnitine, obtained by the chemical resolution of the racemate, crotonobetaine, which is a cheap raw material for the L(−)-carnitine synthesis, is formed.

2) In this process no biochemical substances or other enzymes are to be employed.

3) The cost of incubation and of the raw materials are very low.

The following non-limiting examples illustrate the present invention.

EXAMPLE 1

A 500 ml reaction vessel containing a complex culture medium with crotonobetaine:

| pancreatic peptone | 20 g/l | bidistilled $H_2O$ |
| sodium chloride | 5 g/l | bidistilled $H_2O$ |
| crotonobetaine | 50 m moles/l | bidistilled $H_2O$ |
| pH7 ($\Delta E_{540} = 0.050$) | | | was inoculated with a suspension of *E. coli* 044 K74, previously grown in 5% blood agar, in physiological solution.

The reaction flask was subsequently covered with paraffin oil and incubated at 37° C.

Table 1 shows the L(−)-carnitine formation in relation with the incubation time and the bacteria growth.

TABLE 1 relation between L(—)-carnitine synthesis, incubation time and bacteria growth.

| Incubation time [h] | Growth [$\Delta E_{540}$] | L(—)-carnitine synthesis | |
|---|---|---|---|
| | | L(—)-carnitine [m moles/l] | $\frac{L(-)\text{-carnitine[moles]}}{\text{crotonobetaine[moles]}} \times 10^2$ |
| 0 | 0.0 | — | — |
| 3 | 0.100 | — | — |
| 6 | 0.120 | 0.5 | 0.9 |
| 12 | 0.190 | 2.0 | 3.9 |
| 24 | 0.200 | 6.7 | 13.4 |
| 48 | 0.175 | 6.6 | 13.3 |

EXAMPLE 2

The complex culture medium containing crotonobetaine, inoculated with *E. coli* (example 1), after 24 hrs of incubation was centrifugated at 6000 rounds per minute to separate the grown bacteria. The obtained centrifugate was washed with phosphate buffer according to Sorensen 0.01 M at pH 7.5 (0.20 g/l KH$_2$PO$_4$ and 3.05 g/l Na$_2$HPO$_4$ ·12 H$_2$O), suspended in a 1 l Sorensen phosphate buffer containinq 5 g/l crotonobetaine (34.9 m moles/l) ($\Delta E_{540}=0.080$) and maintained for 24 hrs at 37° C. Subsequently it was again centrifugated and 9.08 m moles/l of L(—)-carnitine were found in the solution. A yield of 26% in relation with crotonobetaine.

EXAMPLE 3

To a complex culture medium containing L(—)-carnitine (31 m moles/l of L-carnitine corresponding to 5 g/l) and inoculated, as in example 1, with several strains of enterobacteria, electron acceptors of the anaerobic respiration and other substances (sodium succinate, sodium fumarate and glucose 10 g/l, potassium nitrate, trimethylamine N-oxide (TMO) 5 g/l) were added.

Table II expresses the yield in moles of γ-butyrobetaine in relation with the L(—)-carnitine utilized.

TABLE II

Influence of the electron acceptors and of other substances on the L(—)-carnitine reduction to γ-butyrobetaine

| Bacteria strains | γ-butyrobetaine formation [% moles] | | | | | |
|---|---|---|---|---|---|---|
| | — | succinate | fumarate | KNO$_3$ | TMO | glucose |
| *Escherichia coli* 044 K74 | 71 | 77 | 13 | 0 | 0 | 0 |
| *Escherichia coli* K12 Hfr H | 45 | 43 | 5 | 0 | 0 | 0 |
| *Salmonella typhimurium* LT$_2$ | 87 | 89 | 68 | 0 | 8 | 71 |
| *Proteus vulgaris* | 79 | 81 | 17 | 0 | 17 | 0 |

EXAMPLE 4

The complex culture medium (KM) described in example 1, or the minimal culture medium (MM) containing:

| | |
|---|---|
| Na$_2$HPO$_4$.12H$_2$O | 15.0 g |
| KH$_2$PO$_4$ | 3.0 g |
| NH$_4$Cl | 1.0 g |
| MgSO$_4$.7 H$_2$O | 0.15 g |
| CaCl$_2$ | 0.014 g |
| FeCl$_3$ | 0.0002 g |
| D-ribose | 7.5 g |
| distilled H$_2$O sufficient for 1 l | | were additioned with 50 m moles of crotonobetaine and with sodium fumarate (10 g/l), potassium nitrate (5 g/l), and trimethylammine N-oxide (5 g/l). They were then incubated with a layer of paraffin (anaerobic conditions) or without paraffin (aerobic conditions), at 37° C. with *E. coil* 044 K74 for 48 hrs.

TABLE III

Influence of electron acceptors on the L-carnitine formation in the growing bacteria

| Culture medium | L(—)-carnitine synthesis [m moles/l] | | | | |
|---|---|---|---|---|---|
| | O$_2$ absence | O$_2$ presence | fumarate | KNO$_3$ | TMO |
| KM | 4.5 | 2.6 | 10.7 | 0.9 | 5.1 |
| MM | 2.7 | 1.5 | 10.8 | 0 | 5.9 |

EXAMPLE 5

A complex culture medium (KM) or a minimal culture medium (MM) containing 50 m moles/l of crotonobetaine were inoculated with *E. coil* 044 K74 and incubated for 48 hrs. The cells, collected and washed twice (example 2), were incubated for 48 hrs in Sorensen buffer containing 50 m moles/l of crotonobetaine to which the electron acceptors were added as in example 4

TABLE IV

Influence of the electron acceptors on the L-carnitine formation with resting cells

| Culture medium | L(—)-carnitine synthesis [m moles/l] | | | | |
|---|---|---|---|---|---|
| | O$_2$ absence | O$_2$ presence | fumarate | KNO$_3$ | TMO |
| KM | 7.5 | 8.3 | 0 | 7.8 | 8.4 |
| MM | 9.1 | 12.1 | 0 | 9.8 | 10.4 |

EXAMPLE 6

Minimal culture mediums (MM), with various crotonobetaine concentrations, supplemented with D-ribose as C source (example 4) were inoculated with *E. coli* 044 K74 (example 1) and incubated at 37° C. for 48 hrs.

TABLE V

L(—)-cartinine synthesis with bacteria grown on minimal culture medium with various crotonobetaine concentrations

| crotonobetaine [m moles/l] | L-cartinine synthesis | | Growth [E$_{540}$] |
|---|---|---|---|
| | L-carnitine moles [m moles/l] | $\frac{\text{L-carnitine moles}}{\text{crotonobetaine moles}} \times 10^2$ | |
| 500 | 5.3 | 1.1 | 0.120 |
| 50 | 4.3 | 8.6 | 0.450 |
| 5 | 0.3 | 6.0 | 0.385 |
| 0.5 | 0.09 | 18.0 | 0.220 |

EXAMPLE 7

A complex culture medium as described in example 1 (A) and a minimal culture medium supplemented with D-ribose, as described in example 4 (B), each containing 8 g/l of L(—)-carnitine, were inoculated with *E. coli* 044 K74. After 48 hrs the collected bacteria, washed twice, were suspended in Sorensen buffer, containing various crotonobetaine concentrations and incubated for 48 hrs a 37° C.

TABLE VI

L(−)-carnitine synthesis with induced resting cells by L(−)-carnitine at various crotonobetaine concentration

| | crotono-betaine [m moles/l] | L-carnitine synthesis | |
|---|---|---|---|
| | | [m moles/l] | $\frac{\text{L-carnitine moles}}{\text{crotonobetaine moles}} \times 10^2$ |
| (A) | 500 | 9.0 | 1.8 |
| | 50 | 7.5 | 15.1 |
| | 5 | 2.9 | 58.4 |
| (B) | 500 | 16.2 | 3.2 |
| | 50 | 8.3 | 16.5 |
| | 5 | 3.7 | 74.0 |

EXAMPLE 8

A complex culture medium containing crotonobetaine as in example 1 inoculated with *E. coli* 044 K74 was centrifugated after 48 hrs. The centrifugate, washed twice, was dispersed in a minimal culture medium, without C and N sources, containing various concentrations of crotonobetaine and incubated for 48 hrs.

TABLE VII

L-carnitine synthesis with resting cells induced by crotonobetaine at various crotonobetaine concentrations

| crotonobetaine [m moles] | L-carnitine synthesis | |
|---|---|---|
| | [m moles/l] | $\frac{\text{L-carnitine moles}}{\text{crotonobetaine moles}} \times 10^2$ |
| 500 | 24.3 | 4.9 |
| 50 | 12.2 | 24.5 |
| 5 | 2.4 | 48.8 |
| 0.5 | 0.47 | 94.0 |

EXAMPLE 9

A minimal culture medium as described in example 4 which contains, instead of crotonobetaine, 50 m moles/1 of L(−)-carnitine was inoculated with *E. coli* 044 K74 and incubated for hrs. Subsequently the collected and twice washed bacteria were incubated at 37° C. in a minimal culture medium without C and N sources but with 50 m moles/1 of crotonobetaine. The optical density at the beginning of the incubation was $\Delta E_{540}=0.210$.

TABLE VIII

L(−)-carnitine formation with resting cells in function of time

| Incubation time [h] | L-carnitine synthesis | |
|---|---|---|
| | [moles/l] | $\frac{\text{L(−)-carnitine moles}}{\text{crotonobetaine moles}} \times 10^2$ |
| 3 | 2.5 | 5.1 |
| 6 | 3.7 | 7.5 |
| 12 | 6.6 | 13.2 |
| 24 | 9.0 | 18.0 |
| 48 | 10.1 | 20.3 |

EXAMPLE 10

A complex culture medium (KM) or a minimal culture medium (MM) without C sources, additioned with the substances indicated in table IX, at the concentrations of 50 m moles/l, was inoculated with *E. coil* 044 K74 and incubated for 48 hrs. Subsequently, the collected bacteria, washed twice with Sorensen buffer, were incubated for 48 hrs in Sorensen buffer with 50 m moles/1 crotonobetaine.

TABLE IX

L-carnitine formation with resting cells in function of the various substances' addition in the growth medium

| | | Growing cells | Resting cells | |
|---|---|---|---|---|
| Medium | added substances | $\Delta E_{540}$ after 48 hrs | $\Delta E_{540}$ at the beginning | L-carnitine systhesis m moles/l |
| KM | — | 0.315 | 0.225 | 1.4 |
| MM | D-Ribose | 0.196 | 0.136 | 0.3 |
| MM | D-Glucose | 0.325 | 0.260 | 0.6 |
| MM | D-Ribose Fumarate | 0.165 | 0.100 | 0 |
| MM | D-Ribose, GABOB+ | 0.395 | 0.220 | 0.3 |
| MM | D-Ribose L-carnitine | 0.255 | 0.190 | 6.6 |

+DL- γ amino β-hydroxybutyric acid.

What is claimed is:

1. A process for producing L(−)-carnitine comprising:
   (a) preparing a bacterial culture medium comprising a crotonobetaine selected from the group consisting of crotonobetaine, a crotonobetaine salt, a crotonobetaine derivative or mixtures thereof;
   (b) inoculating the culture medium with *Escherichia Coli* 044 K 74;
   (c) incubating the bacteria wherein the incubation takes place in anaerobic, partially anaerobic or aerobic conditions wherein the incubation occurs for a time period of 12 hours–120 hours.
   (d) recovering at least 3.9% yeild of L(−)-carnitine from the medium.

2. The process according to claim 1, wherein the crotonobetaine salts are selected from the group consisting of chloride, iodide, perchlorate, nitrate, and phosphate salts of crotonobetaine.

3. The process according to claim 1, wherein the crotonobetaine concentration in culture medium is between 10 $\mu$ moles and 5 moles/1.

4. The process according to claim 1, wherein the bacterial incubation takes place in a commercial complex or minimal nutritive medium, to which are added, to the growing bacteria and/or resting cells, electron acceptors or respiration, hydrogen acceptors and substrates that inhibit the reduction of crotonobetaine to γ-butyrobetaine.

5. The process according to claim 4 wherein the substrates that inhibit the reduction of crotonobetaine to γ-butyrobetaine are selected from the group consisting of oxygen, nitrates, trimetylamine N-oxides, glucose, fructose, saccarose, maltose, dimethylsulphoxide, fumarate, crotonate and acrylate.

6. The process as in claim 1, wherein the incubation occurs for a time period of 12 hours–48 hours.

7. The process according to claim 1 wherein the crotonobetaine derivative is selected from the group consisting of crotonobetaine nitrile, crotonobetaine amide, aryl and alkyl crotonobetaine esters or mixtures thereof.

8. The process according to claim 1, wherein the culture medium is inoculated with induced resting cells and the bacterial culture medium comprises one or more of the group selected from crotonbetaine, and carboxylic esters of crotonobetaine, O-acyl carnitine esters, derivatives of L(−), D(+), and DL-carnitine and salts thereof.

* * * * *